United States Patent [19]

Goldfarb

[11] Patent Number: 4,814,434
[45] Date of Patent: Mar. 21, 1989

[54] INDUCER OF T-SUPPRESSOR CELLS

[75] Inventor: Marcia F. Goldfarb, Portland, Me.

[73] Assignee: Ventres Laboratories, Inc., Portland, Me.

[21] Appl. No.: 653,591

[22] Filed: Nov. 15, 1984

Related U.S. Application Data

[63] Continuation of Ser. No. 576,945, Feb. 3, 1984.

[51] Int. Cl.$^4$ ........................ A61K 35/12; A61K 37/02
[52] U.S. Cl. ................................. 530/380; 530/395;
530/399; 530/413; 530/414; 530/415; 530/837;
435/240.1; 424/93; 424/95; 424/101
[58] Field of Search .................. 530/350, 380; 424/95, 424/101, 88

[56] References Cited

U.S. PATENT DOCUMENTS

| | | |
|---|---|---|
| 3,438,859 | 8/1969 | De Somer . |
| 3,466,367 | 9/1969 | Jaeger . |
| 3,657,417 | 4/1972 | Brunetti . |
| 4,010,148 | 6/1977 | Goldstein . |
| 4,046,877 | 9/1977 | White . |
| 4,077,949 | 3/1978 | Goldstein . |
| 4,082,737 | 4/1978 | McGregor . |
| 4,120,951 | 10/1978 | Goldstein . |
| 4,128,637 | 12/1978 | Naylor . |
| 4,133,804 | 1/1979 | Bach et al. . |
| 4,239,498 | 12/1980 | Rule . |
| 4,250,084 | 2/1981 | Trainin . |
| 4,374,828 | 2/1983 | Folkers et al. . |
| 4,394,374 | 7/1983 | Ushjima . |
| 4,548,813 | 2/1985 | Lawson . |

OTHER PUBLICATIONS

Tada, T. et al., "Advances in Immunology", Dixon ed. 28:1 (1979).
Golub, E. S. "The Cellular Basis of the Immune Response", 2d ed. Chapter 19 (1977).
White, A. "Isolation from Human Plasma of a Protein Fraction with Thymic Hormone-Like Activity", ANN NYAS 332:23 (1979).
Kruisbeeck, A., "Thymic Factors and T-Cell Maturation", Thymus 1:163 (1979).
Remherz, E. L., et al., "The Characterization and Function of Human Immunoregulatory T-Lymph Subsets", Immn. Today (Apr. 1981) pp. 69–74.
Kook, A. I., et al., "Isolation and Partial Chemical Characterization of THF", Cellular Immunology 19:151 (1975).
Shohat, B., et al., "In vitro Induction of T-Suppressor Lymphocytes", 35(1):68 (1983).
Ahmed, A., et al., "T-Lymphocyte Maturation", Annals NYAS 332:81 (1979).
Low, T. L. K., et al., "Current Status of Thymosin Research", Ann NYAS 332:32 (1979).
Bach, J. F., "A New Approach to Immunostimulation", Advances in Pharmacology and Therapeutics, vol. 4 (1979).
Bach, J. F., "The Target Cell of Thymic Hormones", Cell Lineage INSERM Symposium No. 10 (1979).
Lenfant, M., et al., "Relationship Between a Spleen-Derived Immuno-Suppressive Peptide 'SDIP and FTS'", Immunology 48:635 (1983).
Kasakura, S., et al., "Suppressor Cell Induction Factor", Journal of Immunology 130:6 (1983).
Shapira, Z., et al., "Theophylline: A Possible Immunoregulator of T-Cells", Transplantation Proc. 14:(1) (1982).
Goldstein, A., "Current Status of Thymosin and Other Hormones of the Thymus Gland", Recent Prog. in Hormone Res. vol. 37:369 (1981).
Trainin, N., "Thymic Hormones: Inducers and Regulators", Immunology Today 4:(1) (1983).
Mizutani, A., et al., "Effect of Bovine Thymic Hypocalcemic Factor", Chem. Pharm. Bull 25(9):2156 (1977).
Pierschbacher, M. D., "Biological Activity of the Pure Thymus Protein LSH$_r$", ANN NYAS 332:49 (1979).
Schmiege, S., et al., "Immunogenesis from Cultured Marrow and Thymus Cells", Journal of Immunology 113(1):110 (1974).
Eardley, D., et al., "Induction of Specific Suppressor T-Cells in vitro", Journal of Immunology 177:313 (1976).
Miller, H. C., et al., "Modulation of the Immune Response by Antigen-Reactive Lymphocytes", Journal of Immunology 115(3):839 (1975).

Primary Examiner—Delbert R. Phillips
Assistant Examiner—Jeff Kushan

[57] ABSTRACT

A biologically active composition extracted from thymus tissue, capable of inducing immature bone marrow cells to differentiate into competent suppressor T-cells.

8 Claims, No Drawings

INDUCER OF T-SUPPRESSOR CELLS

This application is a continuation of application Ser. No. 576,945, filed Feb. 3, 1984.

FIELD OF THE INVENTION

This invention relates to a new composition of matter, and more particularly to a novel thymic factor isolated in purified form from mammalian thymus tissue which induces immature bone marrow cells to differentiate into competent suppressor T-cells ($T_S$). This novel thymic factor, which can also be called inducer of T-suppressor cells ($iT_S$) is heat stable up to about 80° C. $iT_S$ induces immature bone marrow cells to differentiate into cells which exhibit a phenotypic marker of suppressor T-cells and which when adoptively transferred repress reconstitution of the immune response in irradiated, thymectomized mice. An antibody has also been raised to $iT_S$. This invention also relates to therapeutic methods and fields of use for $iT_S$.

BACKGROUND OF THE INVENTION

The essential role of the thymus gland in the development of immunological competence in animals and man is now generally accepted. In thymectomized animals thymus grafts can restore immunological competence. Findings of this nature have led to the discovery of many different thymic factors. Most of these factors are derived from the thymus gland but some are obtained from serum or thymus epithelial cell cultures. For reviews and general discussion on the nature of thymic factors and how they function in the development of the immune response, see, inter alia, Tada, T. et al *Adv. Immunology* 28, 1 (1979); Golub, E. S. *The Cellular Basis of the Immune Response* Sinauer Mass. 1977, chapter 9; White, A. *Ann. N.Y. Acad. Sci.* 332, 23 (1979); and Kruisbeeck, A. *Thymus* 1 163 (1979).

The mammalian immune system consists of a sophisticated complex of interactive cells and cell products. The immune system develops in the fetus and neonatally, just after birth. Lymphocyte progenitor cells, derived from pluripotential hemopoietic stem cells, first appear in the yolk sac of the developing embryo and in the fetal liver. After birth they are found in the bone marrow, where they persist for life. These lymphocyte progenitor cells are capable of irreversibly differentiating into either of two classes of immunologically competent cells: T-lymphocytes or B lymphocytes. Both classes of lymphocytes are ubiquitous in the blood, lymph, spleen and lymph nodes. T and B lymphocytes appear to be morphologically similar—they are generally small, motile, nonphagocytic cells—yet they bear different immunogenic markers on their plasma membranes and perform distinctly differential immunological functions.

T lymphocytes (hereinafter referred to as T-cells) develop inside the thymus gland from lymphocyte progenitor cells which have migrated through the bloodstream from the bone marrow. Factors with hormone-like effect product inside the thymus apparently induce the progenitor cells to differentiate into functional T-cells with protective or regulatory capcities. Following a maturation process, the T-cells leave the thymus and enter the general blood and lymph circulation.

Some of the progenitor lymphocytes become "helper" T-cells ($T_H$), that is, they interact with the other class of lymphocytes (B-cells) to cause them to mature, divide and become antibody-producing clones. Another subclass of T-cells produced by the thymus is the "suppressor" population ($T_S$). These cells internally regulate the immune system so that only the type and amount of antibody or protective T-cell is produced that is needed. When this suppressor system is not regulated, certain forms of arthritis or autoimmune disease can occur. Yet another subclass of T-cells that arise in the thymus are the so-called "natural killer" T-cells (or $T_{NK}$). These white cells eliminate body cells that have become infected with viruses and other microbes, and they also destroy defective cells such as cancers.

The differentiation of these distinct types of immunologically competent T-cells is controlled by an as yet incompletely understood constellation of thymic factors.

The other class of lymphocytes, called B lymphocytes or B-cells, apparently differentiate inside the bone marrow, liver and spleen from lymphocyte progenitor cells. Then these cells circulate in the bloodstream. The immunological response of mature B cells may be regulated by T-cells or T-cell products. Mature B cells synthesize and secrete immunoglobin antibodies in response to antigenic stimulation. For many antigens, B-cells require the presence of T-helper cells before they can product antibodies. The mechanism of this T-B cooperation is poorly understood, but it is recognized to be inhibited by T-suppressor cells.

The present invention encompasses a thymic factor which causes immature bone marrow cells to become suppressor T-cells. This factor is herein designated inducer of T-suppressor cells, or $iT_S$. This invention also embraces a novel method of purifying the suppressor factor of this invention.

Mammalian bone marrow cells, when incubated with this $iT_S$ factor, become competent suppressor T-cells. It is understood that this capacity of $iT_S$ to induce the effective agents of immunosuppression can be used for therapeutic purposes. For example, human bone marrow cells can be transformed into suppressor T-cells for injection into transplant patients to cause in vivo suppression of foreign tissue rejection. It is also contemplated that pharmaceutical preparations of $iT_S$ can be prepared for direct in vivo inoculation. Naturally occurring autoimmune diseases, which have been correlated with a loss of suppressor cells, may be susceptible to treatment with $iT_S$ factor. Such autoimmune diseases include systemic lupus erythematosus, hemolytic anemia, multiple sclerosis, severe ectopic eczema, hyper-IgE syndrome, and inflammatory bowel disease. See Reinherz, E. L. et al, *Immunology Today* (April, 1981) pp. 69–74. Allergies are also thought to derive from defects in the suppressor T-cell system; hence it is contemplated that $iT_S$ can be of therapeutic use in controlling allergies. And, since loss of the suppressor T-cell population may correlate temporarily with the severity of other clinical diseases, it is further contemplated that $iT_S$ can be used as an adjuvant medication of general utility.

During the past decade a multiplicity of factors which exhibit hormonal activity have been isolated from the mammalian thymus gland. These thymic factors from a remarkably diverse assemblage with respect to the methodologies of their extraction, states of purification, physicochemical properties, and biological activities. Several of these thymic factors have been reported to induce some sort of suppression of the immune system: e.g., anti-thymosin, Thymopoietin I and Thymopoietin II, THF, thymosin $\alpha_7$, FTS, and SDIP. All of these reported thymic suppressor factors have reported molecular weights that are in order of magnitude lower than those measured for applicant's $iT_s$ preparations.

Great Britain Patent Specification No. 1,195,980, published June 24, 1970 described hormone-like preparations derived from thymus gland produced at Yeshiva University, N.Y. The in vivo injection of one such preparation, called anti-thymosin, was reported to inhibit lymphoid tissue proliferation and induce a decrease in the number of blood lymphocytes. This anti-thymosin appeared to have the properties of a protein of molecular weight less than 5000.

U.S. Pat. No. 4,120,951, issued Oct. 17, 1978 to Goldstein and assigned to Sloan-Kettering Institute for Cancer Research, discloses two closely related polypeptides, designated Thymopoietin I and Thymopoietin II, from bovine thymus. The Goldstein patent states that these polypeptides can be used to inhibit the uncontrolled proliferation of thymin-responsive lymphocytes. The molecular weights of Thymopoietin I and II were reported to be around 6,000 to 7,000 daltons.

Kook et al in 1975 reported the isolation of THF, a thymic hormone of molecular weight 3220 and isoelectric point 5.66–5.90. Kook, A. I. et al, *Cellular Immunology* 19: 151 (1975). Shohat et al recently described the induction of T suppressor cells by in vitro treatment of lymphocytes of renal allograph recipients with THF. Shohat, B. et al, *Transplantation* 35 (1): 68 (1983).

Ahmed et al reported that thymosin $\alpha_7$ acts on prothymocytes to induce suppressor cells. Ahmed, A. et al, *Ann. N.Y. Acad. Sci.* 332: 81 (1979). Thymosin $\alpha_7$ has a molecular weight of 2,200 daltons and a pI of around 3.5. Low, T. L. K., et al, *Ann. N.Y. Acad. Sci.* 332: 32 (1979).

Facteur thymique serique (FTS) is a peptide of molecular weight close to 900 that has been isolated from both thymus tissue and normal serum. Bach, J. F., in *Advances in Pharmacology and Therapeutics*, Vol. 4 (Pergamon Press, 1979) p. 145. FTS is reported to activate suppressor T cells in various in vivo and in vitro systems, especially when administered at high pharmalogical dosages. It is reportedly not known whether FTS stimulates mature suppressor cells or induces a maturation of suppressor T cell precursors. Bach, J. F., in *Cell Lineage, Stem Cells and Cell Determination: INSERM Symposium* No. 10, p. 261 (N. LeDouarin, Ed., Elsevier/North-Holland Biomedical Press, 1979).

A spleen-derived immunosuppressive peptide (SDIP) has recently been reported to have physicochemical properties and enzymatic susceptibilities similar to those of the thymic hormone FTS, supra. When injected into sheep erythrocyte (SRBC)-sensitized mice, at the last step of differentiation of the lymphocytes, SDIP reportedly reduced the plaque-forming capacity of spleen cells from the treated animals; a similar inhibitory response was observed with FTS. Lenfant, M. et al, *Immunology* 48: 635 (1983).

U.S. Pat. No. 4,232,498, issued to Rule on Dec. 16, 1980 discloses and claims thymic factors prepared according to a sequential acetone fractionation process. Rule disclosed a suppressor which reportedly repressed reconstitution of the immune response in lethally irradiated thymectomized mice. No physicochemical characterization of this apparently crude thymic extract was presented.

Another suppressor factor has very recently been reported. See Kasakura, S., et al, *The Journal of Immunology* 130 (6): 2720 (June, 1983). The reported physical description of this factor—molecular weight of 18,000–29,000 daltons, pI of 6.2–7.3, and heat resistance only to 56° C.—eliminates the possibility of it being our $iT_s$ factor.

In addition to the above-mentioned thymic suppressor factors, the administration of theophylline has also been reported to activate suppressor T cells from peripheral human blood. Shapira demonstrated a lack of suppressor T-cells in patients with acute rejection episodes (ARE) following kidney transplants. After administration of theophylline-ethyl diamine (aminophylline), the ARE in 12 of 16 patients was abrogated and suppressor T-cells reappeared in their peripheral blood. Shapria, Z. *Transplantation Proceedings* 14 (1): 113 (1982).

It will be noted that the thymic suppressor factors in the prior art discussed above are of comparatively lower molecular weight than $iT_s$. For example the preparation of Example 1 exhibited a measured molecular weight of approximately 65,000 daltons. Indeed, a review of the prior art indicates that most of the thymic factors which have been categorized have molecular weights of less than 10,000 daltons. See, e.g., Goldstein, A. L. et al, in *Recent Progress in Harmone Research*, Vol. 37, p. 369 (Greeb, R. O., Ed., Academic Press, 1981). Furthermore, the lack of homology among those small factors which have been sequenced suggests that they are not cleavage products of a common precursor. Trainin, W., et al, *Immunology Today* 4 (1): 16 (1983).

The few high molecular-weight thymic factors which have been described can be distinguished from $iT_s$ by their biological activities, which tend to enhance rather than suppress immunological competence.

For example, Mizutani et al extracted two purified hypocalcemic proteins, designated $TP_1$ and $TP_2$, from bovine thymus gland. The molecular weight of $TP_1$ was found to be 68,000 daltons and that of $TP_2$ to be 57,000 daltons. Both are heat labile (56° C., 30 min.). Significant increases in antibody-producing cells were found, as indicated by increases in plaque forming cells, when either $TP_1$ or $TP_2$ was injected into neonatal mice. Mizutani et al, *Chem. Pharm. Bull.* 25 (9): 2156 (1977).

White et al obtained a homogeneous protein with thymic hormone-like activity from blood serum. Its molecular weight was determined to be 56,700±300 daltons, and its physical, chemical, and immunological properties indicated an identity with authentic human prealbumin. The biological activities of this high molecular weight compound included inducing an increase in the numbers of sheep erythrocyte plaque-forming cells (IgM) in vitro by spleen cells from neonatally thymectomized mice treated in vivo with the purified compound. White et al, *Annals New York Academy of Sciences* 332: 1 (1979). The use of human serum prealbumin for increasing immunological competence was the subject of U.S. Pat. No. 4,046,877, issued to White et al on Sept. 6, 1977 and assigned to Syntex (U.S.A.) Inc. The data presented in the patent's Example 3 indicates that human prealbumin significantly increased the capacity of spleen cells to synthesize IgM and IgG antibodies, as evidenced by increased numbers of plaque-forming cells.

Pierschbacher et al reported the extraction of a lymphocyte stimulating hormone, denoted LSHr, from beef thymus. LSHr reportedly is a peptide with a molecular weight of 80,000 and an isoelectric point of about 4.55 Administration of microgram quantities of LSHr to nude mice for 2-3 weeks induced development of T-cell function as determined by antibody response to a T-dependent antigen and a response of spleen cells to T-cell mitogen. Ann. N.Y. Acad. Sci. 332: 49 (1979).

Other high molecular-weight thymic factors have been reported by Jin et al, who reportedly extracted a mixture of polypeptides, of molecular weights 9000–68,000 daltons and isoelectric points 5.0–7.5, from pork thymus. Said factors reportedly increase rosette formation in fetal thymocytes, which indicates generally the induction of T-cell differentiation. Jin, T. et al J. Nanking University 1: 115 (1979), cited in Goldstein et al, Recent Progress in Hormone Research, Vol. 37, supra, at p. 381.

The methods employed to extract the above-mentioned factors from thymus tissue typically consist of two general steps. First, a crude extract is prepared from thymus gland—typically by homogenization, heat treatment, centrifugation and filtration. Second, the factor or factors in the crude extract are isolated by enrichment procedures—typically by dialysis, molecular sieve chromatography, affinity chromatography, and/or preparative electrophoresis.

The extraction procedure of the present invention, as will be discussed in greater detail below, also involves a two-part procedure. A crude thymus extract is first prepared in conformance with procedures well known in the art. Said crude extract is then subjected to a novel and surprisingly effective enrichment protocol which for the first time has permitted the isolation of a stable, high molecular-weight T-suppressor factor from mammalian thymus glands.

The crude thymic extract, as used as the start of my inventive process, is prepared in general conformity with the methods described by others; see, e.g., A. Goldstein's Thymic Fraction 2, in U.S. Pat. No. 4,010,148. I then fractionate the crude thymic extract by molecular sieve chromatography and remove contaminants by affinity chromatography using immunoadsorbents.

DETAILED DESCRIPTION OF THE INVENTION

The novel thymic factor ($iT_s$) of the present invention is isolated from mammalian thymus tissue, especially calf thymus. Neonatal vertebrate thymus tissues other than calf thymus are also suitable for the isolation of this factor, but are usually somewhat less available than calf thymus tissue.

The $iT_s$ factor can be isolated by means of the following general procedure. An extract of mammalian thymus is prepared. Said thymus extract is chromatographed by gel filtration on Sephadex G-75 and pooled according to size. The appropriate size pool (70,000–25,000 daltons) is absorbed by solid phase affinity chromatography using an anti-bovine serum albumin column. The unabsorbed fraction is rechromatographed by gel filtration on Sephadex G-75 and pooled according to size. The appropriate size pool (70,000–50,000 daltons) is absorbed by solid phase affinity chromatography using an anti-bovine serum column. The unabsorbed fraction is tested for the presence of $iT_s$ factor by activity assays with murine bone marrow cells.

For example, a crude extract of mammalian thymus tissue is first prepared. Thymus tissue is obtained from freshly slaughtered neonatal vertebrates, preferably from two-week to two-month old calves. It was discovered that the freshly collected thymus glands cannot be frozen for future use without impairing the activity of the $iT_s$ product.

It is preferred procedure to remove extraneous connective and adipose tissues that adhere to the thymus glands. The glands are then minced. It was found convenient to homogenize the minced thymus glands in approximately 200 g aliquots. The minced glands are placed in a two-fold (v/w) excess of homogenization buffer. A suitable buffer for this purpose is 10 mM Tris-HCl, pH 8.0, containing 50 mM NaCl and 0.5 mM $MgCl_2$. The thymus glands are homogenized in the aforementioned buffered saline at high speed for approximately 2 minutes. A suitable homogenization apparatus is a Waring blender. Said homogenization and many of the subsequent steps are carried out at 4° C. in order to slow down protease and other enzymatic activity, and also to inhibit bacterial contamination. An antibiotic was not added because it might affect the subsequent bioassays.

The resulting homogenate is centrifuged for approximately 30 minutes at 12,000×g at 4° C., or until the solid cellular debris has precipitated. The aqueous supernatant is recovered by conventional techniques for further processing. It was observed that any fats on top of the aqueous supernatant will come out later, after heating and the sunbsequent centrifugation; therefore special care need not be taken to remove them at this point.

The recovered aqueous supernatant is heated to approximately 80° C. for 30 to 45 minutes or until the material has congealed. This congealed material consists of denatured proteins, including proteases which might otherwise inactivate the $iT_s$ factor. The congealed solids are then removed by centrifugation for approximately 30 minutes at 12,000×g at 4° C. The aqueous supernatant is collected for further processing; the precipitated pellet is discarded.

The aqueous supernatant is then frozen to −80° C. in order to further denature any proteins which were marginally soluble at higher temperatures. This is also a convenient storage point in the extraction process. I have observed that said aqueous supernatant can be stored at −80° C. for at least 2–3 years without significant impairment of the $iT_s$ activity. It was also found convenient to freeze said aqueous supernatant in 200 ml aliquots, as subsequent purification steps are conveniently carried out with this size of sample.

After thawing at 37° C., e.g. in a water bath, the extract is centrifuged for approximately 30 minutes at 45,000×g at 4° C. This high speed centrifugation serves to remove those marginally soluble proteins which were denatured further by freezing. The resulting supernatant is then concentrated approximately 16-fold by dialysis; e.g., in an Amicon stirred cell fitted with a Y-10 membrane in order to eliminate small molecules of less than, e.g., 10,000 dalton molecular weight. The dialysate containing the low-molecular-weight molecules is discarded.

Those familiar with the field of art to which this invention contributes a novel and unobvious advancement will recognize the above-mentioned preliminary preparatory steps as not departing in significant detail from the protocol of A. Goldstein and others, except that I start with fresh, unfrozen thymus tissue. However, from this point on the method of the present invention departs from the prior art in novel and unobvious ways. The crude extract collected by the above-mentioned preparatory steps is fractionated by two molecular sieve chromatography passages and further refined by absorptions on an anti-bovine serum albumin column and an anti-bovine serum column.

First, the concentrated supernatant from the above-mentioned dialysis step is centrifuged for 15 minutes at 45,000×g at 4° C. in order to remove any remaining solid material which might occlude the gel filtration column. Any precipitate formed at this point is discarded. The supernatant is collected and subjected to molecular sieve chromatography in order to selectively isolate molecules within the 70,000 to 25,000 dalton size range. The preferred method of accomplishing said size fractionation is by gel filtration on Sephadex G-75 (Source: Pharmacia) at 6.8 cm×hr$^{-1}$, using phosphate buffered saline, pH 7.2, without NaN$_3$. Those versed in the art will realize that other gels, e.g. Biogel (Bio-Rad) or Ultragel (LKB), may also be suitably employed to isolate molecules within the specified size range. The 70,000 to 25,000 dalton fractions are pooled and concentrated by dialysis, e.g., in an Amicon stirred cell fitted with a YM-10 membrane, which will pass molecules having molecular weights less than 10,000 daltons.

The 70,000 to 25,000 dalton concentrate is centrifuged for approximately 10 minutes at 1,500×g, in order to remove any proteins which sheared during the concentration step. Any precipitate is discarded. The recovered supernatant is then subjected to affinity chromatography in which rabbit antiserum to bovine serum albumin (BSA) is used as an immunoadsorbent. This immunoadsorbent was selected after I discovered that iT$_s$ has a molecular weight similar to that of the contaminating BSA. Sources of rabbit anti-BSA include Miles Laboratories, Elkhart, Ind. Suitable solid substrata to which rabbit anti-BSA can be bonded include Sepharose-6B (Pharmacia). I prefer to bond the antibody to the solid substratum by means of cyanogen bromide activation of the gel. Passage of the supernatant from the bove-mentioned centrifugation step over the anti-BSA column will result in the physical removal, by adsorption, of contaminating BSA molecules.

The unadsorbed fraction is then subjected to further size fractionation in order to isolate only a 70,000 to 50,000 dalton fraction. This can also be accomplished by gel filtration chromatography on Sephadex G-75 at 3.6 cm×hr$^{-1}$, using sodium azide-free phosphate buffered saline; pH 7.2. The 70,000 to 50,000 dalton fractions are pooled and then concentrated by dialysis, e.g., in an Amicon stirred cell fitted with a YM-10 membrane.

The 70,000 to 50,000 dalton fraction concentrate is centrifuged at approximately 1,500×g for 10 minutes. Any precipitate is discarded.

The recovered supernatant is subjected to further purification by affinity chromatography in which rabbit antiserum to bovine whole serum (BS) (Source: Miles Laboratories) is used as the immunoadsorbent. I have found that the sequence of anti-BSA followed by anti-BS enhances the efficiency of recovery. Albumen is the major contaminant, and taking it out first allows the second size fractionation to be accomplished more easily; other proteins which are minor contaminants are then removed on the anti-BS column.

The unadsorbed fraction from the preceding step should be tested for the presence, concentration, and purity of iT$_s$. Such testing can be accomplished by a combination of physicochemical and biological assays. Physicochemical assays will provide information as to the concentration and degree of homogeneity of the extract. Suitable physicochemical assays to accomplish this purpose include a determination of molecular weight by, e.g., electrophoresis on SDS-PAGE gel; a pI determination by isoelectric focussing on, e.g., agarose or polyacrylamide gel; and a determination of protein content by reading optical density at 280 nm.

Bioassays suitable for confirming the presence of the iT$_s$ factor include assessments of the induction of suppressor T-cell differentiation by, e.g., phenotypic assay for surface antigens characteristic of suppressor T-cells, or by functional assay for suppressor T-cell activity.

The following examples are presented to illustrate the invention but it is not to be considered as limited thereto.

EXAMPLE 1

The preferred method for isolating and purifying the iT$_s$ factor is by means of the following procedure.

1. Thymus glands obtained from freshly slaughtered calves were minced following the removal of connective tissue and other extraneous tissue. The glands were placed in a two-fold (v/w) excess of homogenization buffer (10 mM Tris-HCl, pH 8.0, containing 50 mM NaCl and 0.5 mM MgCl$_2$). The thymus glands were homogenized in a Waring blender for two minutes at maximum output at 4° C., and the resulting homogenate was centrifuged for 30 minutes at 12,000×g at 4° C. The supernatant was heated to approximately 80° C. for 30 to 45 minutes or until the materials had congealed. The solids were removed by centrifugation for 30 minutes at 12,000×g at 4° C. The supernatant was frozen at −80° C. in 200 ml aliquots. After thawing at 37° C., the extract was centrifuged for 30 minutes at 45,00×g at 4° C. The supernatant was concentrated 16-fold in an Amicon stirred cell fitted with a YM-10 membrane.

2. The concentrated supernatant from step 1 was centrifuged for 15 minutes at 45,000×g at 4° C. Any precipitate removed at this point was discarded. The supernatant was fractionated by gel filtration on Sephadex G-75 at 6.8 cm×hr$^{-1}$, using phosphate-buffered saline, pH 7.2, without NaN$_3$. The 70,000 to 25,000 dalton fraction was pooled and concentrated in an Amicon stirred cell fitted with a YM-10 membrane.

3. The 70,000 to 25,000 dalton concentrate was centrifuged for 10 minutes at 1,500×g. Any precipitate was discarded. The supernatant was subjected to affinity chromatography in which rabbit antiserum to bovine serum albumin was used as the immunoadsorbent.

4. The unadsorbed fraction was further fractionated by gel filtration chromatography on Sephadex G-75 at 3.6 cm×hr$^{-1}$, using phosphate buffered saline, pH 7.2, without NaN$_3$. The 70,000 to 50,000 dalton fraction was pooled and concentrated in an Amicon stirred cell fitted with a YM-10 membrane.

5. The 70,000 to 50,000 dalton fraction concentrate was centrifuged at 1,500×g for 10 minutes. Any precipitate formed at this step was discarded.

6. The supernatant from the previous step was subjected to further purification by affinity chromatography in which rabbit antiserum to bovine whole serum was used as the immunoadsorbent. 7. The unadsorbed fraction from the preceding step was tested for protein content, characterized by electrophoretic techniques, and tested by bioassay for the presence of the iT$_s$ factor.

The molecule or molecules contained in the iT$_s$ factor isolated in Example 1 were partially characterized with reference to their physicochemical properties, e.g., protein content, molecular weight, and electrophoretic activity.

Protein content of the $iT_s$ factor was established by measurement of optical density at 280 nm (ISCO UA-5 monitor with a Type 6 optical unit).

The molecular weight of the $iT_s$ factor was determined by two methods, gel filtration and two-dimensional electrophoresis.

Gel filtration was accomplished as described in *Gel Filtration: Theory and Practice* (Pharmacia Fine Chemicals). A Pharmacia column (2.6×98 cm) packed with Sepehdex G-75-120 and equilibrated with phosphate-buffered saline, pH 7.2, without $NaN_3$, was used. The column was run with an upward flow which was maintained with a Technicon Auto Analyzer proportioning pump. A molecular weight of approximately 65,000 daltons was obtained by gel filtration of the $iT_s$ factor isolated in Example 1.

Two-dimensional electrophoresis was also accomplished as described in *Operation of the ISO-DALT System* (Tollaksen, Anderson and Anderson, Argonne National Laboratories, Argonne, Ill., 1981). By this method, the $iT_s$ factor isolated in Example 1 was found to have a molecular weight between 43,000 and 47,000 daltons.

An isoelectric point (pI) of 4.2–4.5 was ascertained by flat bed isoelectric focusing as described in *A Step by Step Guide to Isogel Agarose Isoelectric Focusing* (Marine Colloids).

The biological activity of the $iT_s$ factor isolated in Example 1 was ascertained by means of a phenotypic assay for suppressor T-cells. The $iT_s$ factor was tested for the ability to cause immature mouse prethymocytes from bone marrow to differentiate into suppressor T-cells. The suppressor T-cells were detected by means of a phenotypic assay in which diagnostic surface antigens are detected by antigen-specific monoclonal antibodies.

The Ly2 surface antigen is thought to be a marker for identification of mouse suppressor T-cells, whereas the Ly1 surface antigen is though to be a marker for mouse helper T-cells, See Goblu, E. S., *The Cellular Basis of the Immune Response* (Sinauer Associates, Inc., Sunderland, MA, 1981).

The capacity of $iT_s$ factor to induce suppressor T-cell differentiation was ascertained by the following procedure. Bone marrow cells derived from 9–12 week old BALB/c female mice (Jackson Laboratories, Bar Harbor, ME) were incubated with aliquots of the $iT_s$ factor isolated in Example 1. Bone marrow cells were prepared by the method of Schmeige, S., and H. Miller, *Journal of Immunology* 113: 110 (1974). Approximately $10^7$ bone marrow cells were suspended in 1.0 ml of MEM+10% FBS; an aliquot of $iT_s$ was added; and the sample was incubated for four hours at 37° C. Samples containing $iT_s$ at concentrations ranging from 0.05 to 50 μg/ml were prepared in duplicate sets. Duplicate sets of controls were also prepared, consisting of spleen cells, thymus cells, and bone marrow cells—all without $iT_s$. The control cells were obtained from syngeneic mice as described in *Journal of Immunology* 113: 110 (1974).

After incubation the cells were washed with fresh medium; the cells were centrifuged at approximately 1,000×g, then resuspended in 5 ml of MEM+10% FBS. One set of the samples and controls was treated with monoclonal antibody to Ly2 surface antigen; while the replicate set was treated with monoclonal antibody to LY1 surface antigen. (Source of monoclonal antibodies: Beckin Dickinson, Monoclonal Antibody Center, Sunnyvale, CA). Said monoclonal antibodies were used at a 1:1000 dilution. Each sample and control was incubated for one hour at 4° C. in the presence of monoclonal antibody.

The cells were then washed with fresh medium, and biotinylated horse antiserum to mouse IgG (Source: Miles Laboratories, Cappel Laboratories, Downington, PA) was added. The samples were incubated for an additional hour with the biotinylated antiserum, washed with fresh medium, and treated with fluorisothiocyamate (FITC)-conjugated avidin (Victor Laboratories, Burlingame, CA).

After reacting with FITC-conjugated avidin, the samples were washed and resuspended in fresh medium. Each sample was counted on a cytofluorometer (cytofluorograph 50, Ortho Diagnostics) and the percentage of cells expressing the LY1 or LY2 surface antigens was recorded. The results of this assay are presented in Table I.

TABLE I

| In vitro assay of $iT_s$ for induction of LY2 surface antigen: | | |
|---|---|---|
|  | LY1 | LY2 |
| 50 μg/ml | 5% | 21% |
| 10 μg/ml | 2% | 24% |
| 1 μg/ml | 0% | 17% |
| 0.5 μg/ml | 0% | 8% |
| 0.05 μg/ml | 0% | 0% |
| control, spleen cells | 12% | 8% |
| control, thymus cells | 80% | 92% |
| control, bone marrow cells | 3% | 5% |

Material tested is representative of the $iT_s$ isolated by the process described in Example 1.
Concentrations are given for amount of $iT_s$ incubated per $10^7$ mouse bone marrow cells.
Percentages indicate the number of cells expressing the LY1 or LY2 surface antigens, which are thought to identify mouse helper or suppressor T-cells, respectively.

The maximum expression of LY2 or LY1 in bone marrow cells is approximately 23% in this assay. Such maximum expressions, based on empirical observation, are considered to be due to inherent limitations on the number (approximately 23%) of bone marrow cells which are capable of being induced to become functional suppressor or helper T-cells. The higher values observed in the thymic cell controls are considered to be due to their a priori differentiation within the thymus gland.

The biological activity of the $iT_s$ factor isolated in Example 1 was further ascertained by means of a functional assay for suppressor T-cells. The $iT_s$ factor was tested for the ability to cause immature mouse prethymocyte cells from bone marrow to differentiate into suppressor T-cells. Here the suppressor T-cells were detected by their ability to suppess the murine immune system.

BALB/c female mice were used as syngeneic cell donors and recipients throughout the procedure of this assay. The procedures used to extract, prepare, and incubate the mouse bone marrow cells were identical to those employed in the phenotypic assay, supra.

Approximately $10^7$ mouse bone marrow cells were incubated in culture media (MEM+5% FBS) with various aliquots of $iT_s$ for 4 hours at 37°. Controls consisted of mouse bone marrow cells ($10^7$) incubated with bovine serum albumin in place of $iT_s$.

After incubation, the cells were washed three times in culture media. Approximately $10^7$ of the washed cells were injected in vivo into thymectomized-irradiated (900R) mice. These mice also received by injection either $10^9$ sheep red blood cells (SRBC) to induce suppressor T-cells, or $10^6$ SRBC to induce helper T-cells. See *Journal of Immunology* 117: 313 (1976).

T-cells were obtained for control purposes by adoptively transferring $10^7$ murine thymus cells of the same strain into thymectomized-irradiated (900R) syngeneic recipient mice. These control mice were also injected in vivo with either $10^9$ or $10^6$ SRBC to induce T-suppressor or T-helper cells, respectively.

Five to seven mice were included in each group.

Two or four days later (for T-helper or T-suppressor cells, respectively), $10^6$ spleen cells from said experimental and control adoptive transferee mice were prepared, by the method of H. Miller et al, *Journal of Immunology* 115: 839 (1975). Said suspensions of spleen cells were assigned to $10^7$ normal spleen cell cultures. These were set up according to the method of Miscell and Dutton, as described in *Selected Methods in Immunology*, B. B. Mishell and S. M. Shiigi, eds., Freedman, San Francisco, 1980, pp. 31–37 and 72–77.

The antibody-producing cells were indicated by clear plaques immunologically lysed SRBC. The results of this assay are presented in Table II. The incidence of statistically fewer plaques, or antibody-producing cells, is considered to indicate the suppression of B-cell activity.

TABLE II

In vivo assay of $iT_s$ for suppression of antibody production:

|  | T-Helper ($10^6$-SRBC) | T-Suppressor ($10^9$-SRBC) |
|---|---|---|
| 50 µg/ml | 527 | 148 |
| 10 µg/ml | 810 | 143 |
| 1 µg/ml | 1955 | 235 |
| 0.5 µg/ml | 3090 | 3715 |
| 0.05 µg/ml | 3000 | 3000 |
| control, 200 µg/ml BSA | 0 | 0 |
| control, thymus cells | 7230 | 230 |

Material tested is representative of the $iT_s$ isolated by the process described in Example 1.
Concentrations are given for amount of $iT_s$ incubated per $10^7$ mouse bone marrow cells.
Numbers indicated number of plaques formed.

The premise of this bioassay is that pretreatment of pluripotential bone marrow cells with $iT_s$ will induce their differentiation into competent T-suppressor cells. If so, when said treated bone marrow cells are injected, along with SRBC which serve as antigen templates for antibody formation, into mice whose immune systems have been destroyed, the suppressor T-cells induced by the composition of this invention should act to repress antibody formation to the SRBC antigens. Such immunosuppression is demonstrable in vitro by a relative decrease in plaque forming cells. Note that such immunosuppression is shown here: At concentrations greater than 1.0 µg/ml the $iT_s$ factor reduces the incidence of plaque formation to below that of the maximum number of control thymus cells which are capable of forming plaques. The thymus control cells injected in vivo along with $10^9$ SRBC are considered to represent a baseline equivalent to a mature suppressor system. The BSA controls (no plaque formation observed) indicate that the immune systems of thymectomized-irradiated recipient mice had indeed been totally destroyed prior to this reconstitution experiment.

EXAMPLE 2

Antibodies to $iT_s$ were prepared by the following procedure: Rabbits were injected subcutaneously with an emulsion of $iT_s$ and complete Freund's adjuvant (1:1). After one month, secondary injections with $iT_s$ and incomplete Freund's adjuvant were given subcutaneously. The animals were bled after 9–11 more days. Subsequent boosts (secondary injections) and bleeds were carried out at 14–18 days and 9–11 days, respectively. Antibodies specific for the $iT_s$ factor were isolated from serum by conventional means well known to those versed in the serological art.

Said isolated antibodies were shown to be specific for $iT_s$ in the following manner. The antibodies were bound to an affinity chromatography column, using materials and methods similar to those described in Example 1, and used as an immunoadsorbent to separate their specific binding partners from a crude thymic extract, prepared as in Example 1. Bound molecules were eluted with 4M MgCl. The isolated molecules were assayed by physicochemical assays and two bioassays, exactly as described in Example 1. The results of those assays indicated that the $iT_s$ factor had been selectively and specifically isolated from crude thymic extract by means of this preparatory process.

EXAMPLE 3

The $iT_s$ factor isolated by the process described under Example 1 or Example 2 is used to therapeutically suppress the immune system of an allograft recipient. Bone marrow cells from the potential transparent recipient are incubated in vitro with $iT_s$ to maximize the induction of T suppressor cells. Said $T_s$ cells are then returned to the transplant recipient, where they naturally suppress an immunological reaction to the new tissue.

I claim:

1. A process for extracting from mammalian vertebrate thymus tissue a factor capable of inducing immature bone marrow cells to differentiate into competent suppressor T-cells, the steps of which comprise:

A. preparing a crude buffered aqueous thymus extract from thymus glands, which ave not been frozen," of freshly slaughtered neonatal mammalian vertebrates;

B. fractionating said crude thymus extract to isolate a 70,000 to 25,000 dalton molecular size fraction;

C. contacting said 70,000 to 25,000 dalton molecular size fraction with an immunoadsorbent containing antiserum to bovine serum albumin;

D. fractionating the unadsorbed material from step C to isolate a 70,000 to 50,000 dalton molecular size fraction;

E. contacting said 70,000 to 50,000 dalton molecular size fraction with an immunoadsorbent containing antiserum to bovine whole serum; and F. collecting the unadsorbed material from step E.

2. A process as in claim 1 in which the crude buffered aqueous thymus extract of step A is prepared as follows:

A. removing connective and adipose tissues from thymus glands, which have not been frozen, obtained from freshly slaughtered neonatal vertebrates;

B. homogenizing said thymus glands in a buffered solution;

C. treating the homogenate to remove cellular debris;

D. heating the liquid separated in step C to approximately 80° C. until soluble proteins, including proteases, have congealed;
E. removing said congealed material;
F. freezing the uncongealed liquid separated in step E;
G. thawing the product of step F and removing any solids;
H. concentrating the product from step G to a molecular size range larger than 10,000 daltons; and
I. recovering the concentrate of greater than 10,000 dalton molecular size.

3. A process for extracting from thymus tissue a factor capable of inducing immature bone marrow cells to differentiate into competent T-cells, the steps of which comprise:
A. raising antibodies specific to the inducer factor isolated by the process of claim 1;
B. bonding said specific antibodies to a gel chromatography column to form an immunoadsorbent;
C. passing a crude thymic extract over said immunoadsorbent;
D. washing away unbound materials;
E. eluting the bound inducer factor from the immunoadsorbent.

4. A biological composition extracted from thymus tissue which has not been frozen and was obtained from a freshly slaughtered neonatal vertebrate, which composition is heat stable to 80° C. and has been extracted from the specific portion of said tissue which falls in the 70,000 to 25,000 dalton molecular size range, which composition is further characterized by its capability at a concentration of at least 1 µg/ml of specifically inducing immature bone marrow cells to differentiate into competent suppressor T-cells, its capability in a concentration of at least 1 µg/ml, when added to $10^7$ bone marrow cells from BALB/c female mice in vitro and incubated for about 4 hours, of inducing a portion of said cells to differentiate into T-suppressor cells which express Ly-2 antigen and its capability to suppress the murine immune systems of said mice, as demonstrated by an in vitro assay carried out by the steps comprising;
injecting thymectomized-irradiated (900 R) BALB/c female mice with $10^7$ pluripotential mouse bone marrow cells from said mice which have been preincubated for at least 4 hours at about 37° with at least 1 µg/ml of said biological composition and then injecting from about $10^6$ to about $10^9$ sheep red blood cells;
removing $10^6$ spleen cells from said mice from about two to four days after injecting said mice, as stated, with said treated bone marrow cells and sheep red blood cells and adding the cells so removed to a culture of about $10^7$ normal mouse spleen cells;
culturing the resultant cell mixture;
assaying said culture for the formation of antibodies to sheep red blood cells by counting the number of plaques (antibody producing cells) in said culture; and
comparing the results to those obtained from an otherwise identical procedure wherein said mice are first injected with about $10^7$ mouse bone marrow cells which have been preincubated under the same conditions with bovine serum albumin instead of said biological composition.

5. The biological composition according to claim 4 wherein said ability of inducing bone marrow cells from BALB/c female mice to differentiate to T-suppressor cells is demonstrated by a phenotypic assay comprising the steps of:
incubating $10^7$ bone marrow cells from 9-12 week old BALB/c female mice treated with at least 1 µg/ml of said biological composition for about 4 hours at about 37° C.;
adding to said cells monoclonal antibody by Ly 2 surface antigen;
incubating said cells with said monoclonal antibody for about 1 hour at 4° C.;
adding biotinylated horse antiserum to mouse IgG to said cells;
incubating for about one additional hour;
treating said cells with fluoroisothiocyanate (FITC)-conjugated avidin;
counting the number of cells expressing Ly 2 surface antigen; and
comparing the result to those obtained with and culture of $10^7$ bone marrow cells from syngeneic mice that has been treated identically except that none of said biological composition has been added.

6. A therapeutic composition comprising a pharmaceutically effective amount of a composition as described in claim 4 or 5 admixed with an appropriate pharmaceutical vehicle.

7. A biological composition capable, at a concentration of at least 1 µg/ml, of inducing immature bone marrow cells to differentiate into competent suppressor T-cells, prepared by the process of any of claim 1, claim 2 or claim 3.

8. A therapeutical composition comprising a pharmaceutically effective amount of a biological composition capable, at a concentration of at least 1 µg/ml of inducing immature bone marrow cells to differentiate into competent suppressor T-cells, prepared by the process of any of claim 1, claim 2, or claim 3.

* * * * *